(12) United States Patent
He et al.

(10) Patent No.: US 11,083,496 B2
(45) Date of Patent: Aug. 10, 2021

(54) FRACTURE REDUCTION SYSTEM

(71) Applicant: HANGZHOU SANTAN MEDICAL TECHNOLOGY CO., LTD, Zhejiang (CN)

(72) Inventors: Bin He, Zhejiang (CN); Shuogui Xu, Zhejiang (CN); Rui Tong, Zhejiang (CN); Yu Wu, Zhejiang (CN)

(73) Assignee: Hangzhou Santan Medical Technology Co., LTD, Hangzhou (CN)

( * ) Notice: Subject to any disclaimer, the term of this patent is extended or adjusted under 35 U.S.C. 154(b) by 29 days.

(21) Appl. No.: 16/136,129

(22) Filed: Sep. 19, 2018

(65) Prior Publication Data

US 2019/0150985 A1    May 23, 2019

(30) Foreign Application Priority Data

Nov. 21, 2017  (CN) .......................... 201711168015.9

(51) Int. Cl.
| | | |
|---|---|---|
| *A61B 17/64* | (2006.01) | |
| *A61B 17/62* | (2006.01) | |
| *A61B 90/00* | (2016.01) | |
| *A61B 17/16* | (2006.01) | |

(52) U.S. Cl.
CPC ............ *A61B 17/645* (2013.01); *A61B 17/62* (2013.01); *A61B 90/36* (2016.02); *A61B 17/1626* (2013.01); *A61B 17/6425* (2013.01)

(58) Field of Classification Search
CPC ... A61B 17/645; A61B 17/6491; A61B 17/64; A61B 17/6408; A61B 17/66
See application file for complete search history.

(56) References Cited

U.S. PATENT DOCUMENTS

| | | | | |
|---|---|---|---|---|
| 2012/0330312 A1* | 12/2012 | Burgherr | ................ | A61B 17/66 606/54 |
| 2014/0236153 A1* | 8/2014 | Edelhauser | ............ | A61B 17/66 606/56 |
| 2018/0055569 A1* | 3/2018 | Wahl | ...................... | A61B 34/10 |

* cited by examiner

*Primary Examiner* — Julianna N Harvey
(74) *Attorney, Agent, or Firm* — Dragon Sun Law Firm, PC; Jinggao Li, Esq.

(57) ABSTRACT

A fracture reduction system includes a reduction device for reducing a fracture bone to be reduced; and a display device for displaying a posture of the fracture bone to be reduced based on a bone model. The display device can cooperate with the reduction device so that the bone model moves synchronously with the fracture bone to be reduced. The posture of the fracture bone to be reduced is displayed based on the bone model, so that the medical staff can know the current posture of the fracture bone to be reduced according to the posture of the bone model and design corresponding reduction actions specifically according to the reduction conditions, so as to reduce the difficulty and increase the precision of fracture reduction.

7 Claims, 7 Drawing Sheets

FRACTURE REDUCTION SYSTEM

CROSS-REFERENCE TO RELATED APPLICATIONS

This application is related to and claims priority to Chinese Patent Application Serial Number 201711168015.9, filed Nov. 21, 2017, and entitled Fracture Reduction System, the entirety of which is incorporated herein by reference.

BACKGROUND OF THE INVENTION

Field of the Invention

The present application relates to the terminal technical field, especially to a fracture reduction system.

Description of the Related Art

In the present medical technology, when bone closed reduction is needed, the position relation between the bones is determined through an X ray firstly; then the reduction path of the bones is determined according to the position relation obtained from the X ray; and then the reduction path is adjusted through doctor's manipulation or temporary external fixation, thereby fracture reduction is achieved.

BRIEF SUMMARY OF THE INVENTION

According to an embodiment of the present application, a fracture reduction system is provided. The system includes a reduction device for reducing the fracture bone to be reduced. The system also includes a display device for displaying a posture of the fracture bone to be reduced based on a bone model. Of note, the display device can cooperate with the reduction device, so that the bone model moves synchronously with the fracture bone to be reduced.

Optionally, the bone model includes a virtual bone model constructed based on the feature parameters of the fracture bone to be reduced. The display device includes a display module, which is used to display the virtual bone model.

Optionally, the bone model includes a solid bone model formed according to the feature parameters of the fracture bone to be reduced and the degrees of freedom of the display device are not less than those of the reduction device; and the directions of degrees of freedom of the display device include those of the reduction device.

Optionally, the reduction device includes a detection module, which is used for detecting the movement data of the fracture bone to be reduced, wherein the movement data can be sent to the display device so that the display device can update the posture of the bone model according to the movement data.

Optionally, either one of the reduction device and the display device can receive a first movement instruction and send it to the other for corresponding posture adjustment.

Optionally, the first movement instruction can be input by an instruction input module of either of the display device and the reduction device or the first movement instruction can be sent through a third party apparatus to either of the display device and the reduction device.

Optionally, the reduction device and the display device can respectively receive a second movement instruction and respectively conduct a corresponding posture adjustment according to the second movement command.

Optionally, the reduction device includes a first power input end, and the display device including a second power input end mechanically connected to the first power input end. The power input for the first power input end can be used to realize movement of the reduction device in at least one direction of degree of freedom, and the power input for the second power input end can be used to realize movement of the display device corresponding to the at least one direction of degree of freedom.

Optionally, the first power input end and the second power input end are connected through a flexible shaft.

Optionally, the reduction device and the display device can be self locked in each direction of degree of freedom respectively.

The technical solution provided by the embodiment of the present application can have the following beneficial effects:

It can be known from the above embodiment that the fracture reduction system can conduct posture display of the fracture bone to be reduced based on the bone model, so that the medical staff can know the current posture of the fracture bone to be reduced according to the posture of the bone model and design corresponding reduction actions specifically according to the reduction conditions, so as to reduce the difficulty of fracture reduction and increase the precision of fracture reduction.

It shall be understood that the above general description and the following details are only illustrative and explanatory and cannot limit the present application.

BRIEF DESCRIPTION OF THE SEVERAL VIEWS OF THE DRAWINGS

The drawings here are incorporated into the description and form a part of the present description, illustrating the embodiment of the present application and explaining the principles of the present application along with the description.

DETAILED DESCRIPTION OF THE INVENTION

Figure 1:
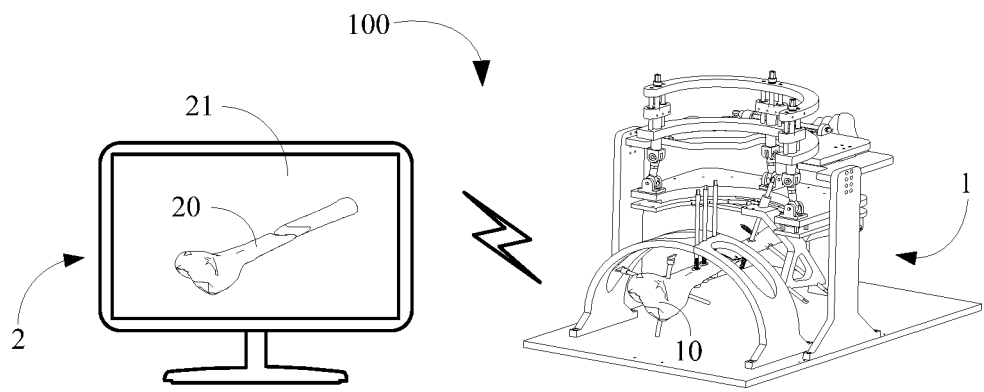
FIG. 1 is a schematic diagram of a fracture reduction system according to an exemplary embodiment.

Here the exemplary embodiment is explained in detail (it is indicated in the drawings). When the following description relates to the drawings, unless otherwise noted, the same numbers in different drawings represent identical or similar elements. The implementation method in the following exemplary embodiment does not represent all the methods consistent with the present application. On the contrary, they are only examples of some devices and methods that are consistent with the present application in some aspects as stated in the attached claims.

The terms used in the present application are only used to depict a specific embodiment, rather than define the present application. In the present application and the attached claims, unless otherwise noted, "a", "said", and "the" with single forms also include their plural forms. It shall also be understood that "and/or" used in this description refers to any or all possible combinations of one or more related items.

It shall be noted that although the present application may adopt terms such as first, second, third etc. for different kinds of information, these terms do not limit the information. They are only used to distinguish information of the same type. For example, within the range of the present application, the first information can also be called the second information, and in the same way, the second information can be called the first information. According to the context, the word "if", e.g., may be explained as "when" or "in response to".

FIG. 1 is a schematic diagram of a fracture reduction system according to an exemplary embodiment. As shown in FIG. 1, the fracture reduction system 100 can include a reduction device 1 and a display device 2, wherein the reduction device 1 can be fixedly connected to a fracture bone to be reduced 10 in an affected limb, so as to the fracture bone to be reduced 10 is reduced by the reduction device 1; the display device 2 can display a posture of the fracture bone to be reduced 10 based on a bone model 20, so that the medical staff can know the current posture of the fracture bone to be reduced 10 according to the posture of the bone model 20, which facilitates the design of corresponding reduction action according to the reduction conditions so as to lower the difficulty of the fracture reduction and improve the accuracy thereof. In details, cooperation between the display device 2 and the reduction device 1 enables the synchronous movement between the fracture bone to be reduced 10 and the bone model 20, so as to display the posture of the fracture bone to be reduced 10 by the bone model 20.

For example, assuming that the fracture bone to be reduced 10 includes first bone and second bone in dislocation, the bone model 20 can include first bone model 20 and second bone model 20 in dislocation, and the dislocation status between the first bone model 20 and the second bone model 20 is the same as that of the first bone and the second bone, when the reduction device 1 is adjusted so that the first bone moves relative to the second bone, the first bone model 20 can perform the same movement relative to the second bone model 20 and thus produce the same displacement vector based on cooperation between the reduction device 1 and the display device 2, so as to observe the reduction of the fracture bone to be reduced 10 outside the body through the display device 2. The displacement vector can include an angular displacement vector and a linear displacement vector.

It shall be noted that the synchronous movement between the fracture bone to be reduced 10 and the bone model 20 only defines the fracture bone to be reduced 10 and the bone model 20 to produce the same displacement vector based on the same reference coordinate system and does not define on the temporal sequence. For example, the posture adjustment on the fracture bone to be reduced 10 by the reduction device 1 and the posture adjustment on the bone model 20 by the display device 2 may be simultaneous; or the posture adjustment on the bone model 20 by the display device 2 can be conducted any interval after the posture adjustment on the fracture bone to be reduced 10 by the reduction device 1. This is not limited by the present application.

In one embodiment, still as shown in FIG. 1, a bone model 20 can include a virtual bone model 20 constructed based on the feature parameters of the fracture bone to be reduced 10, so that the corresponding display device 2 can include a display module 21, which can be used to display the above virtual bone model 20. For example, the display device 2 can be a computer terminal, projection terminal or other terminals with a projection function, which is not limited by the present application. The feature parameters of the fracture bone to be reduced 10 can be obtained through CT scanning of the fracture bone to be reduced 10, and the corresponding virtual bone model 20 can be obtained through three-dimensional reconstruction software.

Figure 2:
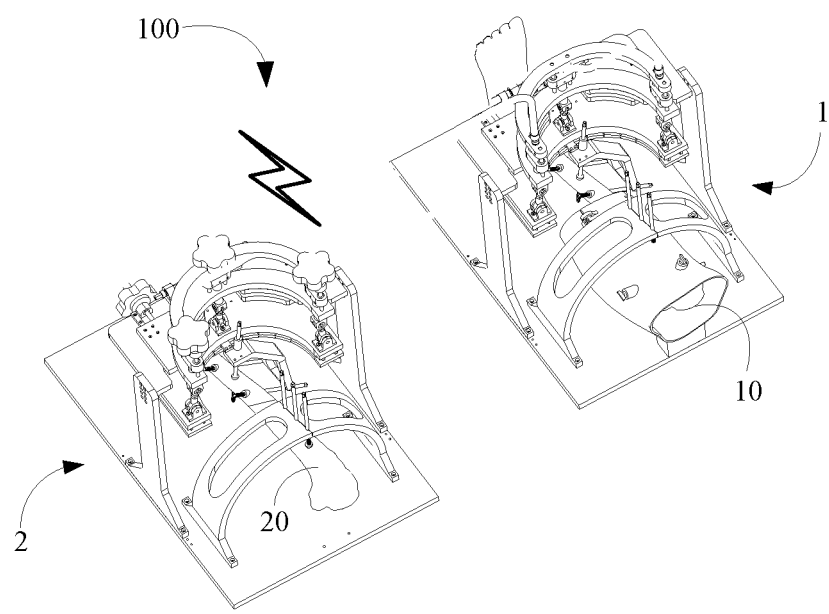
FIG. 2 is a schematic diagram of another fracture reduction system according to an exemplary embodiment.

In another embodiment, as shown in FIG. 2, a bone model 20 can include a solid bone model 20 formed based on the feature parameters of a fracture bone to be reduced 10, so that the corresponding display device 2 can be the mechanical structure in fixed connection to the solid bone model 20 as shown in FIG. 2. Wherein, the solid bone model 20 is a solid structure made through three-dimensional printing. Specifically, the fracture bone to be reduced 10 can be CT scanned in advance; the virtual bone model 20 can be reconstructed through the obtained scanning data, and then the virtual bone model 20 is printed by three-dimensional printing.

In this embodiment, the display device 2 has a number of degree of freedom not less than that of the reduction device 1, and the directions of degree of freedom of the display device 2 include those of the reduction device 1, so as to ensure that when the reduction device 1 is used for posture adjustment of the fracture bone to be reduced 10, the display device 2 can be used for posture adjustment of the bone model 20 along the same direction of degree of freedom.

For example, assuming that the reduction device 1 has 4 degrees of freedom based on an absolute coordinate system XOY, the 4 degrees of freedom are movement along an X axis, rotation about the X axis, movement along a Y axis, and rotation about the Y axis. Correspondingly, the display device 2 has at least 4 degrees of freedom based on the absolute coordinate system XOY, and the at least four degrees of freedom shall include movement along the X axis, rotation about the X axis, movement along the Y axis, and rotation about the Y axis. When the reduction device 1 is adjusted to move the fracture bone to be reduced 10 along the X axis, the bone model 20 can also be moved along the X axis based on cooperation between the reduction device 1 and the display device 2, so as to realize posture display of the fracture bone to be reduced 10.

In the fracture reduction system described in above embodiment, there are a variety of coordination ways between the reduction device 1 and display device 2, so that the bone model 20 can move synchronously with the fracture bone to be reduced 10 in the reduction device 1.

Figure 3:
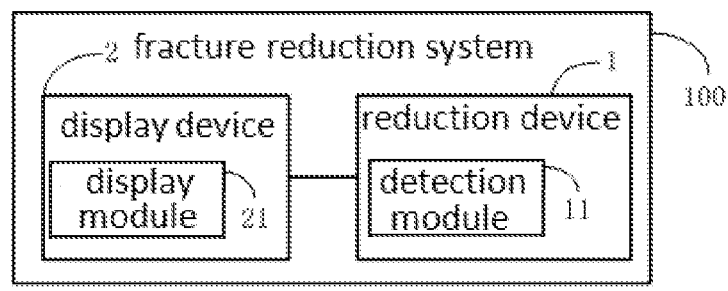
FIG. 3 is a structure block diagram of a fracture reduction system according to an exemplary embodiment.

In one embodiment, as shown in FIG. 3, the movement of the fracture bone to be reduced 10 can be monitored. For example, the reduction device 1 can include a detection module 11, which can be used to detect movement data of the fracture bone to be reduced 10. The movement data can be sent to the display device 2, so that the display device 2 can update the posture of the bone model 20 according to the movement data. Of course, the movement data can also be obtained by user in some other embodiments, the user can manually control the display device 2 according to the movement data, so that the bone model 20 can produce a corresponding posture variation.

As the fracture bone to be reduced 10 is fixed to the reduction device 1, the detection module 11 can obtain the movement data of the fracture bone to be reduced 10 along the corresponding direction of degree of freedom by detecting the movement data of the reduction device 1. Again, taking the absolute coordinate system XOY as an example, assuming that when the reduction device 1 is driven to move along the X axis, the fracture bone to be reduced 10 is also moved along the X axis, thereby the movement displacement of reduction device 1 along the X axis detected by the detection module 11 is the movement displacement of the fracture bone to be reduced 10 along the X axis. Further, the movement data can be sent to the display device 2 based on the data connection established between the reduction device 1 and the display device 2, so that the display device 2 can update the posture of the bone model 20 based on the movement displacement, so as to ensure that when the next reduction action is conducted on the fracture bone to be reduced 10, the fracture bone to be reduced 10 and the bone model 20 have the same posture, which ensures the precision of fracture reduction. The detection module 11 can include sensors, such as linear displacement sensor, angular displacement sensor, speed sensor, counter etc., and the present application has no limitation in this regard. The number of the detection modules 11 can be equal to that of the degrees of freedom of the reduction device 1.

In another embodiment, either of the reduction device 1 and the display device 2 can receive a first movement instruction, and send the first movement instruction to the other one for posture adjustment.

Figure 4:
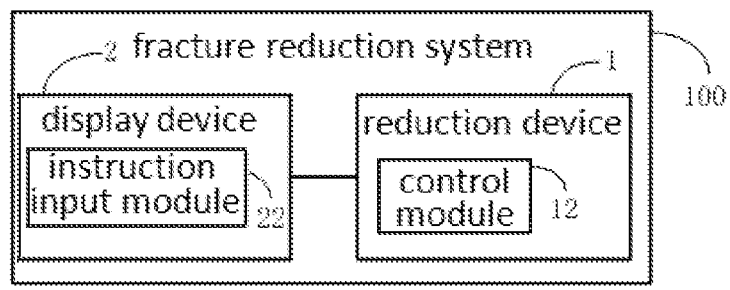
FIG. 4 is a structure block diagram of another fracture reduction system according to an exemplary embodiment.

For example, as shown in FIG. 4, assuming that the display device 2 includes an instruction input module 22, through which the first movement instruction can be input, and that the reduction device 1 can include a control module 12, when the first movement instruction generated by the display device 2 is sent to the control module 12 of the reduction device 1 based on the data communication between the display device 2 and the reduction device 1, the control module 12 can control the reduction device 1 to generate movement corresponding to the first movement instruction, so as to reduce the fracture bone to be reduced 10. The instruction input module 22 can be a GUI or software on the display device 2, and the present application does not have limitation in this regard.

Further, the movement data of the fracture bone to be reduced 10 can be detected by the detection module 11 and fed back to the display device 2, so that the display device 2 can adjust the posture of the bone model 20 according to the movement data, enabling adjustment of the bone model 20 based on the real-time posture of the fracture bone to be reduced 10; or else, the first movement instruction generated in the display device 2 directly controls the bone model 20 for posture adjustment, so as to avoid multiple times of communication between the reduction device 1 and the display device 2 to improve reduction efficiency.

Figure 5:
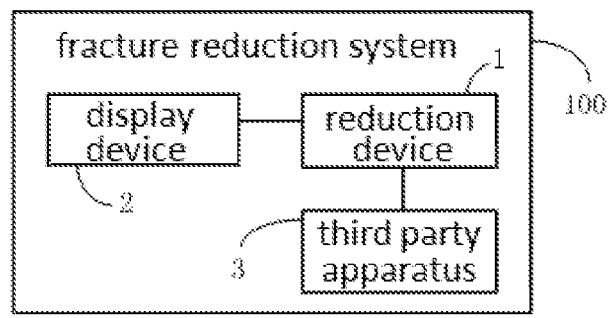
FIG. 5 is a structure block diagram of another fracture reduction system according to an exemplary embodiment.

For another example, as shown in FIG. 5, assuming that the display device has a form of using the mechanical structure as shown in FIG. 2 for the fracture reduction system, the system can further include a third party apparatus 3 capable of communication with the reduction device 1. The user can input the first movement instruction based on the third party apparatus 3, and the first movement instruction can be sent to the reduction device 1 side. The reduction device 1 can on one hand adjust the posture of the fracture bone to be reduced 10 based on the first movement instruction, and on the other hand send the first movement instruction to the display device 2 side, so that the display device 2 can update the posture of bone model 20 based on the first movement instruction. The third party apparatus 3 can be an operation end separating from the reduction device 2, e.g., an operation handle or a mobile terminal and the like, and the present application has no limitation in this regard.

Figure 6:
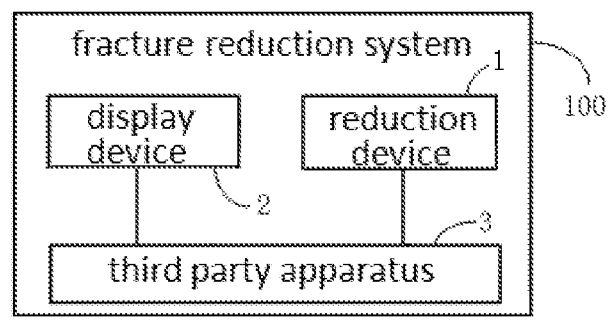
FIG. 6 is a structure block diagram of another fracture reduction system according to an exemplary embodiment.

In another embodiment, the reduction device 1 and the display device 2 can respectively receive a second movement instruction, and respectively conduct posture adjustment according to the second movement instruction. For example, as shown in FIG. 6, assuming that the third party apparatus 3 can simultaneously communicate with the reduction device 1 and the display device 2, the second movement instruction input from the third party apparatus 3 by the user can be simultaneously sent to the reduction device 1 side and the display device 2 side, so that the reduction device 1 and the display device 2 can respectively adjust the posture of the fracture bone to be reduced 10 and the bone model 20 based on the second movement instruction, which facilitates the intelligent development of the fracture reduction and reduces human cost.

Figure 7:
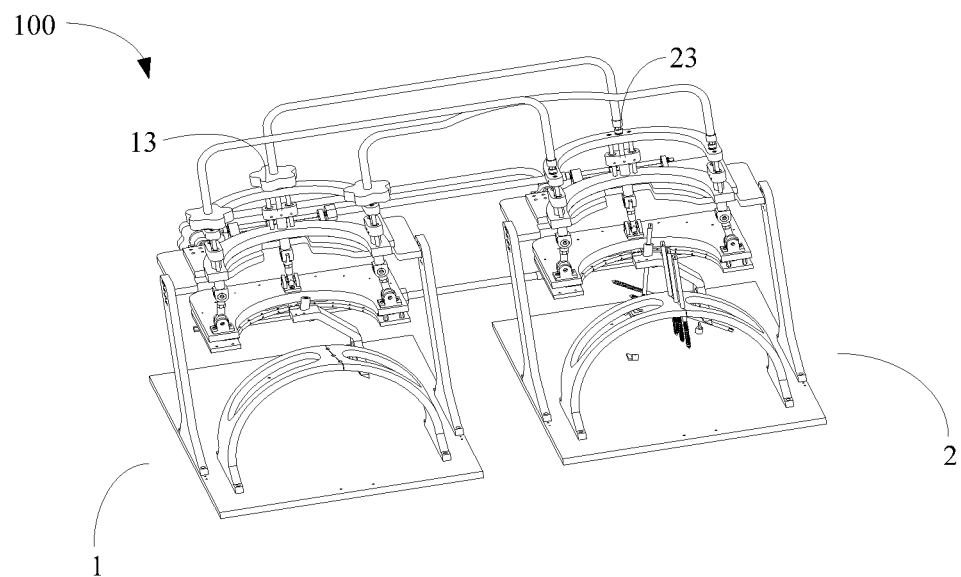
FIG. 7 is a schematic diagram of another fracture reduction system according to an exemplary embodiment.

Apart from cooperation between the reduction device 1 and the display device 2 through data communication in the above embodiments, based on the embodiment shown on FIG. 2, the reduction device 1 and the display device 2 can also be mechanically connected to realize synchronous movement between the fracture bone to be reduced 10 and the solid bone model 20. For example, as shown in FIG. 7, assuming that the reduction device 1 can include a first power input end 13, when power input is conducted for the first power input end 13, movement of the reduction device 1 in at least one direction of degree of freedom can be realized. similarly, the display device 2 can include a second power input end 23, and when power input is conducted for the second power input end 23, movement of the display device 2 in at least one direction of degree of freedom corresponding to the first power input end 13 can be realized, so that when the first power input end 13 and the second power input end 23 are mechanically connected, if any of them is driven into movement, the other one connected can conduct a synchronous movement. For example, the first power input end 13 and the second power input end 14 can be connected through a flexible shaft, so that when any of the first power input end 13 and the second power input end 14 is driven into movement, power is transmitted through the flexible shaft to the other one to drive it into movement synchronously.

The reduction device 1 can conduct self locking in at least one direction of degree of freedom, and the display device 2 can also conduct self locking in the direction of degree of freedom corresponding to the at least one direction of degree of freedom, so as to maintain the current posture of the fracture bone to be reduced and the bone model, which facilitates targeted design of the next reduction action. The at least one direction of degree of freedom can include any direction of degree of freedom based on the coordinate system XOY, e.g. movement along the X axis, rotation about the Y axis, etc. The present application has no limitation in this regard.

Figure 8:
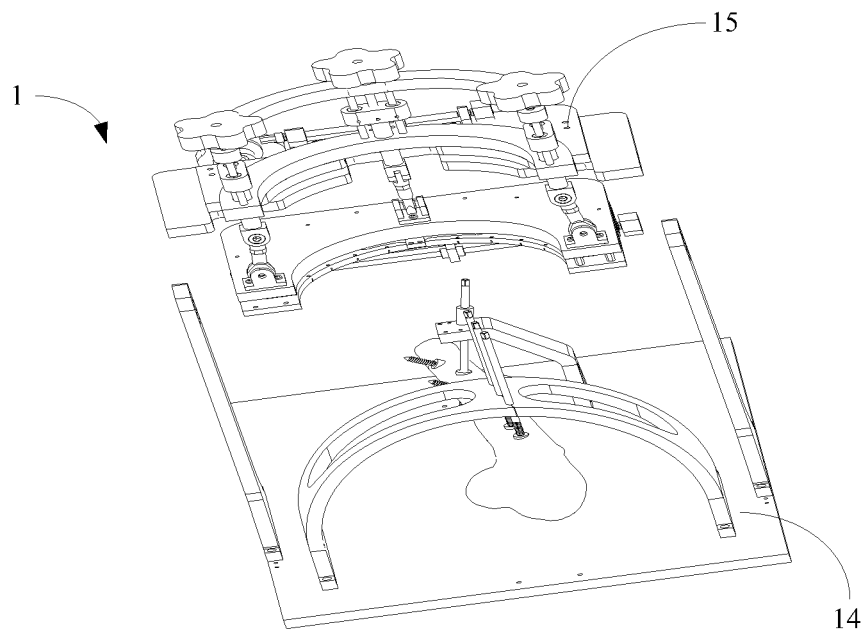
FIG. 8 is a decomposition schematic diagram of a reduction device according to an exemplary embodiment.

Based on the technical solution of the present application, the reduction device can adopt the mechanical structure as shown in FIG. 7. And the reduction device 1 can conduct reduction adjustment of the fracture bone to be reduced 10 along six directions of degree of freedom. As shown in FIG. 8, the reduction device 1 can include a fixing structure 14 for fixing the fracture bone to be reduced 10 and a reduction execution structure 15 for cooperation with the fixing structure 14, so that when in movement, the reduction execution structure 15 can drive the fixing structure 14, and realize the reduction of the fracture bone to be reduced 10 along six directions of degrees of freedom through the reduction device 1.

Figure 9:
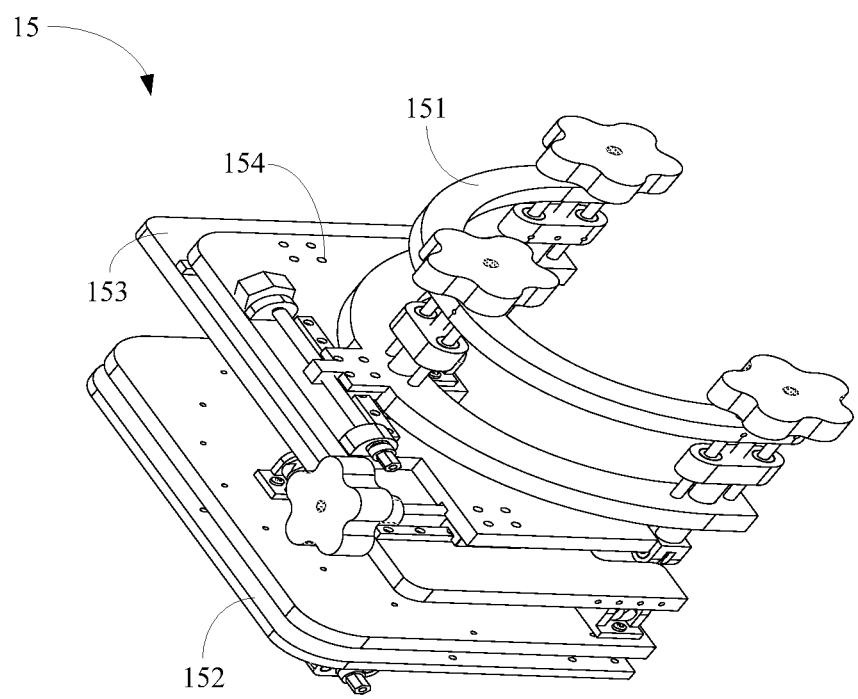
FIG. 9 is a schematic diagram of a reduction execution structure according to an exemplary embodiment.

In this embodiment, as shown in FIG. 9, the reduction execution structure 15 can include a first moving part 151, a second moving part 152, a third moving part 153, and a fourth moving part 154 connected to the fixing structure 14. The movement of the reduction device 1 along six directions of degree of freedom can be realized by cooperation between the first moving part 151, the second moving part 152, the third moving part 153, the fourth moving part 154, and the fixing structure 14.

Figure 10:
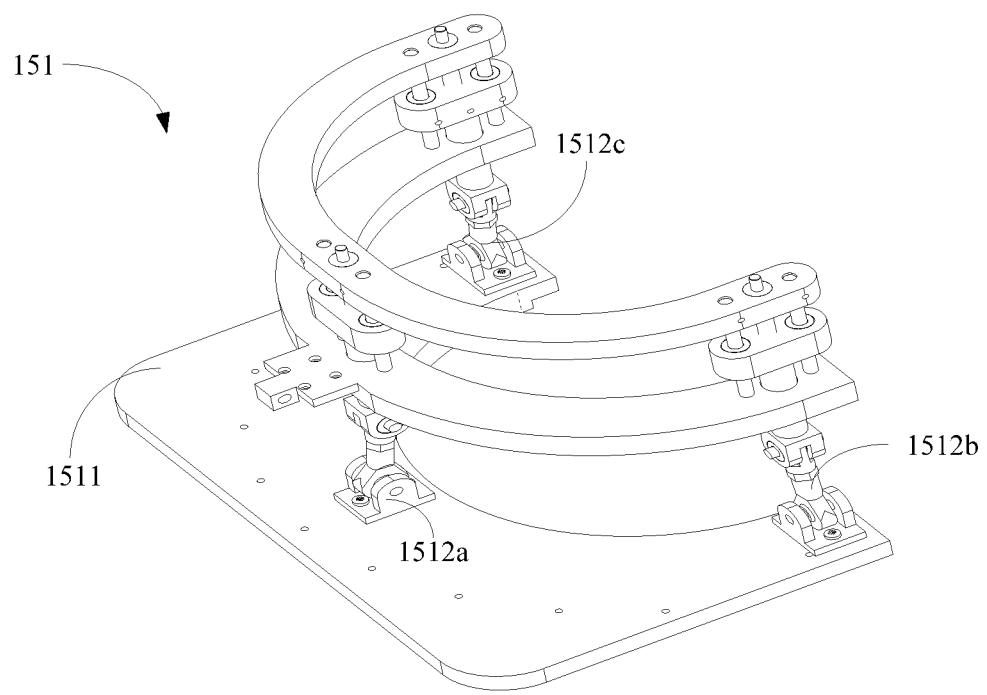
FIG. 10 is a structure schematic diagram of a first movement part according to an exemplary embodiment.
Figure 11:
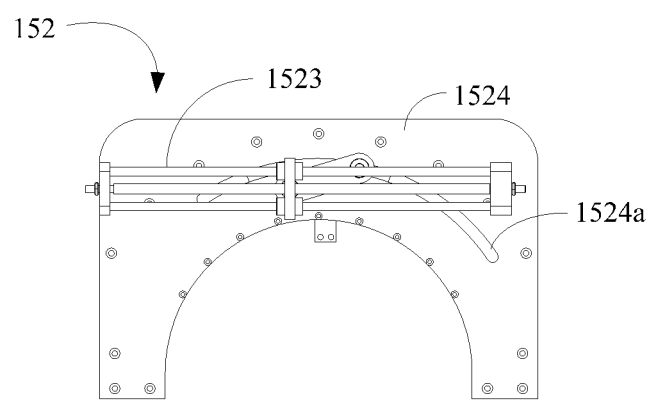
FIGS. 11-13 are structure schematic diagrams of a second movement part according to an exemplary embodiment.
Figure 12:
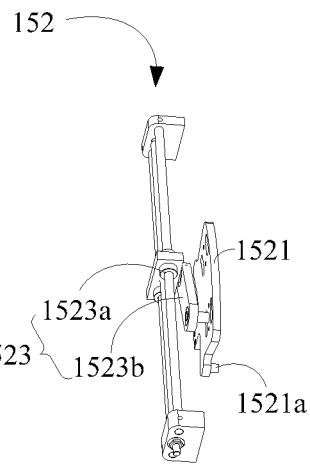
Figure 13:
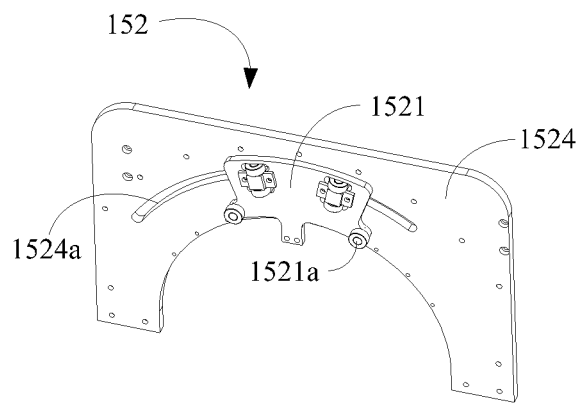
Figure 14:
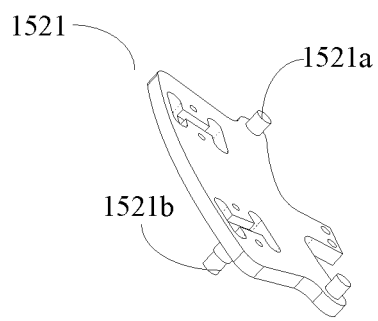
FIG. 14 is a structure schematic diagram of a guide block according to an exemplary embodiment.

As shown in FIG. 10, the first moving part 151 can include a first fixing seat 1511 connected to the fixing structure 14 and a plurality of first driving structures 1512 connected to the first fixing seat 1511, e.g. 1512a, 1512b, 1512c etc. shown on FIG. 10. When the plurality of first driving structures 1512 are in synchronous movement, the first moving part 151 can be driven as a whole to move translationally along a first axis I, so that the fixing structure moves along the first axis I translationally, and further, the translational movement of the fracture bone to be reduced 10 along the first axis I can be realized. When each of first driving structure 1512 is articulated to the first fixing seat 1511, the first moving part 151 can be driven to rotate about a second axis II or a third axis III when the plurality of first driving structures 1522 are in non-synchronous movement, wherein the first axis I, the second axis II, and the third axis III are perpendicular to each other.

As shown in FIG. 10, relative rotation of the first moving part 151 about the second axis II can be realized when the first driving structure a is fixed and the first driving structures b and c are moving in the opposite directions simultaneously. Further, relative rotation of the first moving part about the third axis III can be realized when the first driving structures b and c are fixed and the first driving structure a is in movement.

In this embodiment, as shown in FIGS. 11-14, the first fixing seat 1511 can be fixed to the fixing structure 14 by a second moving part 152, wherein the second moving part 152 includes a guiding block 1521 in fixed connection to the fixing structure 14, and the guiding block 1521 can include a first guiding protrusion 1521a. The first fixing seat 1511 including a first guiding groove (not shown in the figures) in cooperation with the first guiding protrusion 1521a, wherein the first guiding protrusion 1521a can cooperate with the first guiding groove to make the guiding block 1521 rotate relative to the first axis I.

Specifically, for example, the second moving part 152 can further include a second driving structure 1523 and a second fixing seat 1524 in fixed connection to the first fixing seat 1511. The guiding block 1521 further includes a second guiding protrusion 1521b. The second guiding protrusion 1521b and the first guiding protrusion 1521a are respectively located at both sides of the guiding block 1521, and the second fixing seat 1524 can include a second guiding groove 1524a for cooperation with the second guiding protrusion 1521b, and the second guiding protrusion 1521b can penetrate the second guiding groove 1524a for connection to the second driving structure 1523, so that when movement of the second driving structure 1523 drives the second guiding protrusion 1521b to move in the second guiding groove 1524a, the guiding block 1521 can be driven to rotate relative to the first axis I with the guiding action of the first guiding groove.

The second driving structure 1523 can include a connecting rod 1523b and a power element 1523a. One end of the connecting rod 1523b is in rotational connection to the second guiding protrusion 1521b, and the other end is in rotational connection to the power element 1523a, so as to drive the guiding block 1521 rotate relative to the first axis I when the power element 1523a moves translationally along an axis parallel to the second axis II. The power element 1523a can adopt the form of a mechanical structure, e.g., it can include a sliding block in rotational connection to a connecting rod and a screw in threaded connection to the sliding block, so that when the sliding block is reciprocating on the screw, it can drive the reduction device 1 to rotate about the first axis I.

Figure 15:
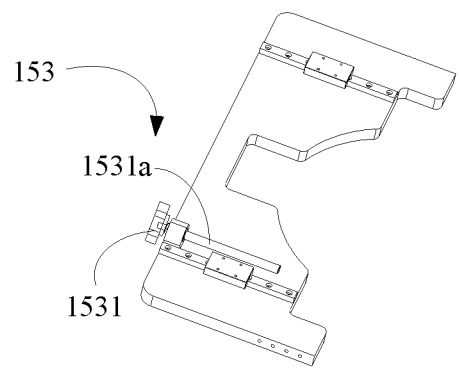
FIG. 15 is a structure schematic diagram of a third movement part according to an exemplary embodiment.
Figure 16:
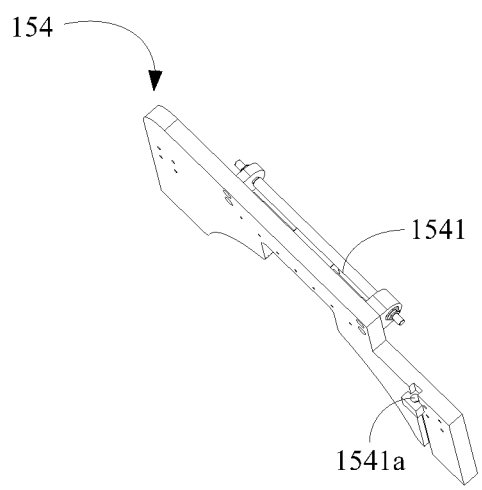
FIG. 16 is a structure schematic diagram of a fourth movement part according to an exemplary embodiment.

Further, in order to realize movement of the reduction device along the first axis I and the second axis II, as shown in FIGS. 15-16, the third moving part 153 in the reduction execution structure 15 can be fixed to the fixing structure 14, the fourth moving part 154 is in sliding connection to the third moving part 153, and the for the fourth moving part 154 is in fixed connection to the fixing structure 14 through the first moving part 151. The third moving part 153 can include a third driving structure 1531, through which the third moving part 153 is driven to slide along the second axis II relative to the fourth moving part 154, so as to further move the fixing structure 14 translationally along the second axis. The third moving part 154 can include a fourth driving structure 1541, through which the fourth moving part 154 is driven to translate along the third axis III, so as to further move the fixing structure 14 translationally along the second axis.

The third driving structure 1531 and the fourth driving structure 1541 can be basically the same structure, in this case the third driving structure 1531 as an example. As shown in FIG. 15, the third driving structure 1531 may include a screw 1531a, and the fourth moving part 154 is provided with a threaded hole 1541a matched with the screw 1531a, thereby driving a fourth moving part 154 relative to the third moving part 153 to translate towards the second axis II direction when rotating screw 1531a.

Of course, in the fracture reduction system as shown in FIG. 2, the display device 2 can adopt the same mechanical structure as the reduction device 1 to save processing time. In addition to the mechanical structure with six degree of freedom described above in the above embodiment, the mechanical structure of the reduction device 1 can also adopt other reduction structures for fracture reduction, and the present application does not have a limitation in this regard.

After considering the description and applying the disclosure, a person skilled in the art could easily conceive of other implementations of the present application. The present application aims to cover any variation, use, or adaptive change, which comply with the general principle of the present application and include the common knowledge and conventional technical means in the art not disclosed by the present application. The description and embodiments are only illustrative, and the extent and spirit of the present application are pointed out by the following claims.

It shall be understood that the present application is not limited to the above described precise structure shown in the drawings and can have amendments and variations within the extent, which is defined only by the attached claims.

We claim:

1. A fracture reduction system, comprising:
a bone model configured to be correlated with a fractured bone to be reduced in an affected limb based upon feature parameters of the fractured bone to be reduced;
a bone model display communicatively coupled to a reduction device adapted for fixed connection to the fractured bone to be reduced, wherein the reduction device is used for posture adjustment of the fractured bone to be reduced and the bone model display is used for posture adjustment of the bone model along a same direction of one or more degrees of freedom of the fractured bone to be reduced, the bone model display displaying a visualization of the bone model with a same posture of the fractured bone to be reduced by the posture adjustment of the bone model and the fractured bone to be reduced, wherein the bone model display communicates with the reduction device so that the bone model moves synchronously with the fractured bone to be reduced to produce a same displacement vector based a same reference coordinate system with the fractured bone to be reduced.

2. The fracture reduction system according to claim 1, wherein the bone model is a solid bone model formed based on the feature parameters of the fractured bone to be reduce; wherein the one or more degrees of freedom of the bone model display are not less than those of the reduction device, and the directions of the one or more degrees of freedom of the bone model display include those of the reduction device.

3. The fracture reduction system according to claim 2, wherein the reduction device receives a first movement instruction and sends the first movement instruction to the bone model display for corresponding posture adjustment.

4. The fracture reduction system according to claim 3, wherein the first movement instruction is input by an instruction input module of one of the bone model display, the reduction device and a third party apparatus.

5. The fracture reduction system according to claim 4, wherein the bone model display adjusts the posture of the bone model according to movement data of the fractured bone to be reduced, enabling adjustment of the bone model based on real-time posture of the fractured bone to be reduced.

6. The fracture reduction system according to claim 5, wherein the reduction device comprises a detection module for detecting movement data of the fractured bone to be reduced, wherein the movement data is sent to the bone model display so that the bone model display updates the posture of the bone model according to the movement data.

7. The fracture reduction system according to claim 2, wherein the bone model display receives a first movement instruction and sends the first movement instruction to the reduction device for corresponding posture adjustment.

* * * * *